United States Patent [19]

Davis et al.

[11] Patent Number: 4,585,436

[45] Date of Patent: Apr. 29, 1986

[54] PERITONEAL DIALYSIS APPARATUS

[75] Inventors: Ralph Davis, Burlington, Wis.; Marc Bellotti, Winnetka; Arthur Lueders, Mundelein, both of Ill.

[73] Assignee: Baxter Travenol Laboratories, Inc., Deerfield, Ill.

[21] Appl. No.: 548,390

[22] Filed: Nov. 3, 1983

[51] Int. Cl.[4] .............................................. A61M 1/00
[52] U.S. Cl. ........................................ 604/29; 604/4; 604/34; 604/83
[58] Field of Search .......................................... 604/4–6, 604/27–29, 33–34, 249–250, 80–81, 83, 174, 283, 410, 280; 285/150

[56] References Cited

U.S. PATENT DOCUMENTS

| | | | |
|---|---|---|---|
| 1,020,123 | 3/1912 | Brampton et al. | 285/155 |
| 1,929,434 | 10/1933 | Kocher | 184/7 |
| 2,562,967 | 8/1951 | Teglund | 285/210 |
| 2,658,776 | 10/1953 | Wilcox | 287/54 |
| 2,838,320 | 6/1958 | Hill | 287/54 |
| 2,885,226 | 5/1959 | Mueller | 285/231 |
| 3,078,848 | 2/1963 | Milbert | 128/251 |
| 3,157,201 | 11/1964 | Littman | 137/525.47 |
| 3,366,143 | 1/1968 | Bauer | 137/798 |
| 3,463,517 | 8/1969 | Courtot et al. | 285/93 |
| 3,486,771 | 12/1969 | Conlin | 285/39 |
| 3,526,419 | 9/1970 | Saguchi | 285/334.1 |
| 3,823,737 | 7/1974 | Szymanski | 137/607 |
| 3,872,863 | 3/1975 | Lasker et al. | 604/34 |
| 3,916,948 | 11/1975 | Benjamin | 604/250 |
| 3,957,082 | 5/1976 | Fulson | 137/625.41 |
| 4,062,569 | 12/1977 | Kay | 285/4 |
| 4,096,859 | 6/1978 | Agarwal et al. | 604/28 |
| 4,130,303 | 12/1978 | George | 285/137 |
| 4,190,047 | 2/1980 | Jacobsen et al. | 604/29 |
| 4,239,041 | 12/1980 | Popovich et al. | 604/28 |
| 4,240,408 | 12/1980 | Schael | 604/28 |
| 4,257,416 | 3/1981 | Prager | 604/28 |
| 4,379,452 | 4/1983 | De Vries | 604/6 |
| 4,381,003 | 4/1983 | Buoncristiani | 604/6 |
| 4,425,113 | 1/1984 | Bilstad | 604/6 |
| 4,425,116 | 1/1984 | Bilstad et al. | 604/6 |

Primary Examiner—C. Fred Rosenbaum
Assistant Examiner—Michelle N. Lester
Attorney, Agent, or Firm—Paul C. Flattery; Daniel D. Ryan; Garrettson Ellis

[57] ABSTRACT

Automated peritoneal dialysis apparatus for providing dialysis solution to a patient and including bracket means for receiving and holding a multiple junction connector of a flexible conduit set member carried by the apparatus. The bracket means is adapted to hold the multiple junction connector in only a single position of orientation whereby flexible conduits of the set member extending from the connector are naturally directed toward their intended destination stations.

10 Claims, 6 Drawing Figures

PERITONEAL DIALYSIS APPARATUS

TECHNICAL FIELD AND PRIOR ART

This application relates to improvements in apparatus for providing peritoneal solution to a patient in an automated manner.

Automated peritoneal dialysis solution apparatus are known to the art, being illustrated for example by Agarwal et al. U.S. Pat. No. 4,096,859, Tirkkonen U.S. Pat. No. 3,783,866, and Lasker et al. U.S. Pat. No. 3,872,863.

Basically, the peritoneal dialysis apparatus provides a preprogrammed administration of typically warmed peritoneal solution to the peritoneal cavity of a patient in desired quantities, and then permits it to be withdrawn at a predetermined time. Several different peritoneal dialysis therapies, for example CCPD and IPD, can be provided by the use of apparatus of this type.

As a disadvantage, automated peritoneal dialysis apparatus is cumbersome. Generally, large quantities of dialysis solution are required, typically being provided by a number of large bags of solution. There is typically a heater bag in which the dialysis solution is heated individual aliquots. There is tubing leading to and from the patient and between the bags, and also there is likely to be a drain/weigh bag, and also a large waste dialyzate bag. plus the tubing interconnecting all parts. As the result of this, as a disposable dialysis solution set is removed from its package, the use of prior designs faces a great tangle of lines and bags which must be installed onto the hardware apparatus, with the risk that the confusing array of lines and bags can be incorrectly installed onto the apparatus, with undesirable consequences.

In accordance with this invention an improvement is provided which greatly facilitates the installation of interconnected bags and tubing of the flexible conduit set member which is carried by the hardware apparatus, and through which the solution passes so that the user can easily install the set member onto the hardware apparatus without confusion and error of installation. Also, a significant decrease in the amount of tubing necessary for the flexible conduits is provided when compared with many prior art configurations, for a significant cost savings, and conventional solution containers may be attached to the set member of this invention for simplification of use and reduction of cost of the set member.

DESCRIPTION OF THE INVENTION

The automated peritoneal dialysis apparatus may have a solution supply station, a dialysis solution heating station, dialysis solution volume measuring station, in which the volume of solution may be measured indirectly by its weight, a pump station for moving the dialysis solution, and valve means for controlling dialysis solution flow around the apparatus.

In accordance with this invention, bracket means may be provided for receiving and holding a multiple junction connector, such as an X connector, of a flexible-conduit set member carried by the apparatus. The bracket means may be adapted to hold the multiple junction connector in only a single position of orientation, with the results that flexible conduits of the set member extending from the multiple junction connector are naturally directed toward their intended destination stations. While the four channel X connector is preferred, other multiple junction connectors of three, five, or more intersecting channels may also be used in this invention. For convenience of usage, the term "X connector" is intended to include other multiple junction connectors as equivalents thereto.

Preferably, the bracket means may define a plurality, typically at least three, pins of differing diameter to pass through corresponding apertures of a mounted X connector for retention thereof in a single position of orientation. The pins may define enlarged outer ends to provide snap-fit retention for a mounted X connector.

The pump station used in this invention may define track means for installing a plurality of separate tubing sections of the set member, and a single pump rotor member for simultaneously pumping fluid through the tubing sections. One of the tubing sections passing through the pump station may communicate between the X connector and the solution supply station, while the other of the tubing sections passing through the pump station may communicate between the dialysis solution volume measuring station and a drain. The drain may be large drain container such as a drain bag, or the tubing may simply pass ot an open drain, as may be desired.

Additionally, the hardware apparatus of this invention may be used in conjunction with a flexible-conduit set member which may contain peritoneal solution and which may be disposable, being made of plastic material. The flexible-conduit set member may include flexible tubing communicating with the X connector, with one or more flexible solution containers attached to the flexible tubing, if desired. Other flexible tubing also communicates with other branches of the X connector and terminates in coupler members, which may, for example, be simple medical connecting spikes, or may be more complex couplers such as threaded couplers of known design or the like. One of the other flexible tubings may define at least two connected branch tubings which also terminate in coupler members of the type described above. The first-mentioned flexible tubing or the attached container may also define a branch tubing extending therefrom.

The way such a flexible-conduit set member can be used in accordance with this invention, and the advantages thereof, is described below.

The X connector described above may define flange means, the flange means defining, in turn, a plurality of apertures of differing size, to permit installation of the multiple junction connector on a bracket of the peritoneal dialysis hardware apparatus, typically of the type described herein, in only a single position of orientation. Pins of the bracket of the peritoneal hardware apparatus pass through the apertures to retain the X connector on the bracket in the single position of orientation.

The pins may define enlarged outer ends to provide snap-fit retention for a mounted X connector, and may be disposed in a triangular pattern.

The pump station may define multiple track means for installing in opposed relation separate tubing sections of theset member, and a single pump rotor member for simultaneously pumping fluid through both of the tubing sections.

One of the flexible tubins or a connected branch tubing of the flexible tubing set may be connected to a manifold tube, the manifold tube being connected at its other end to a one-piece molded plastic manifold. A plurality of manifold branch tubes are connected to the plastic manifold, with the manifold branch tubes terminating in coupler members and carrying flow clamps. Thus, access connections to a large plurality of solution containers may be provided.

DESCRIPTION OF SPECIFIC EMBODIMENT

Figure 1:
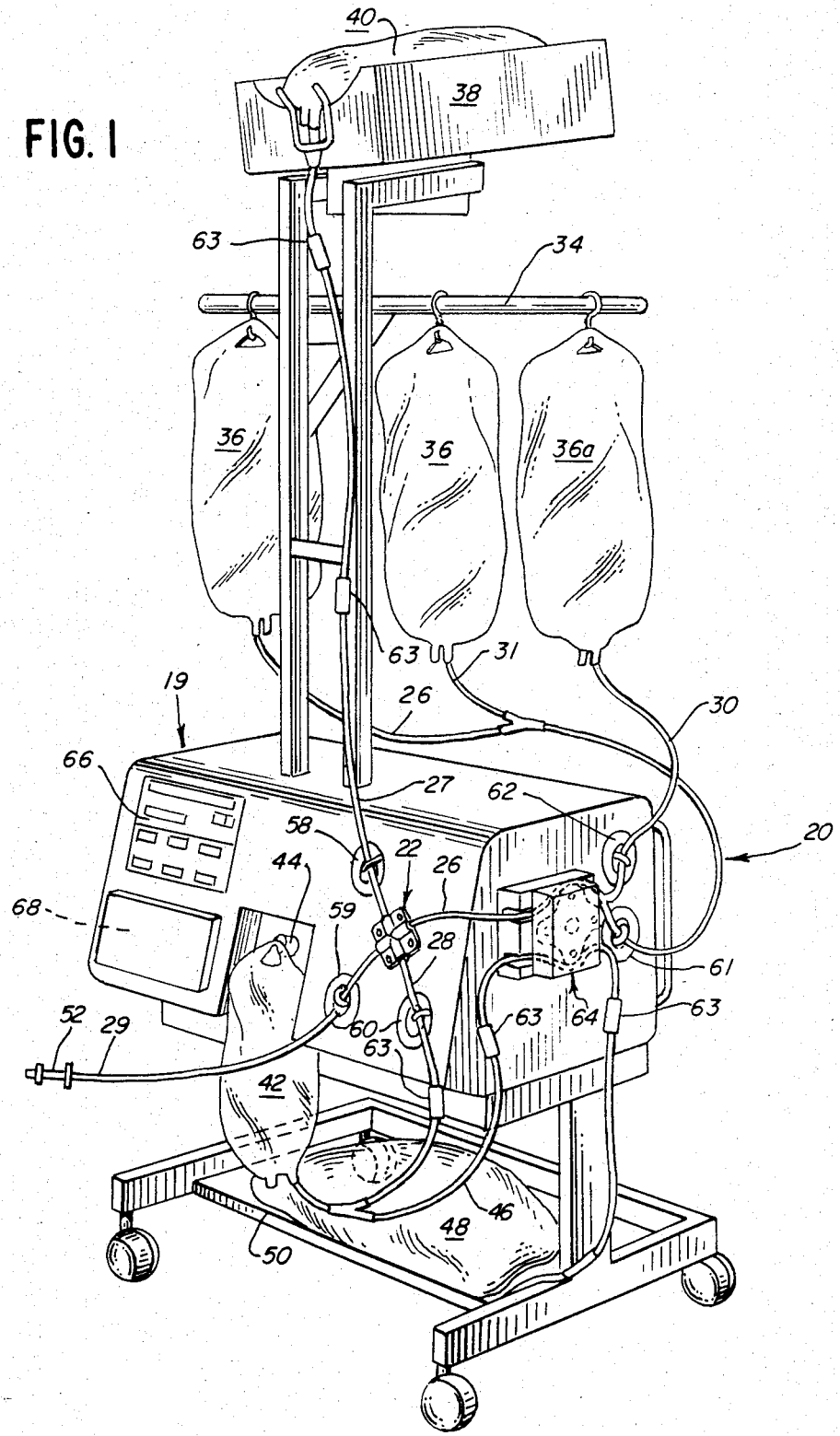
FIG. 1 is a perspective view of peritoneal dialysis apparatus, having a flexible-conduit container and set member carried thereon.

Referring to FIGS. 1-6, FIG. 1 shows peritoneal dialysis apparatus 19 of this invention with a flexible-conduit container and set member 20 carried thereon. At the heart of set 20 is X connector 22 which, as particularly shown in FIGS. 2, 3 and 6, may be a molded plastic piece with four interconnected conduits 24 which respectively communicate in sealed relation with first through fourth flexible tubings 26-29. Thus the flexible tubings are all interconnected and in common flow relationship by means of X connector 22.

Flexible tubing 26 defines a pair of branch tubins 30, 31, each of tubings 26, 30, 31 terminating in a conventional spike connector 32. Flexible tubing 26 is directed by its orientation from X connector 22 toward a rack 34 on dialysis apparatus 19 which carries dialysis solution bags 36, 36a in hanging relationship, thus serving as the solution supply station. Flexible tubings 26, 31 are spiked into bags 36 while bag 36a, intended to be the last bag of solution used in the dialysis process, communicates with flexible tubing branch 30.

Flexible tubing 27 is directed by X connector 22 upwardly to the dialysis solution heating station 38, which may include an electrical resistance heater to heat solution bag 40 as it resides on station 38. A thermostat may also be present to control the temperature to the desired level, plus a scale or load cell to weigh the contents of bag 40.

Flexible tubing 28 may communicate between X connector 22 and bag 42, which may be integrally attached to the rest of the set, and which may be carried in a dialysis solution volume measuring station at electronic scale member 44. As shown in FIG. 1 bag 42 may hang on electronic scale member 44 for electronic readout of the weight of the bag, from which the volume of dialysis solution present in bag 42 may beinferred.

Branch conduit 46 may communicate between bag 42 of tubing 28 and a drain directly, or with drain bag or other container 48 carried on lower shelf member 50 of the machine 19. Conduit 46 terminates in a spike-receiving connector 47 to receive a spike from the drain bag or an extension set.

Figure 6:
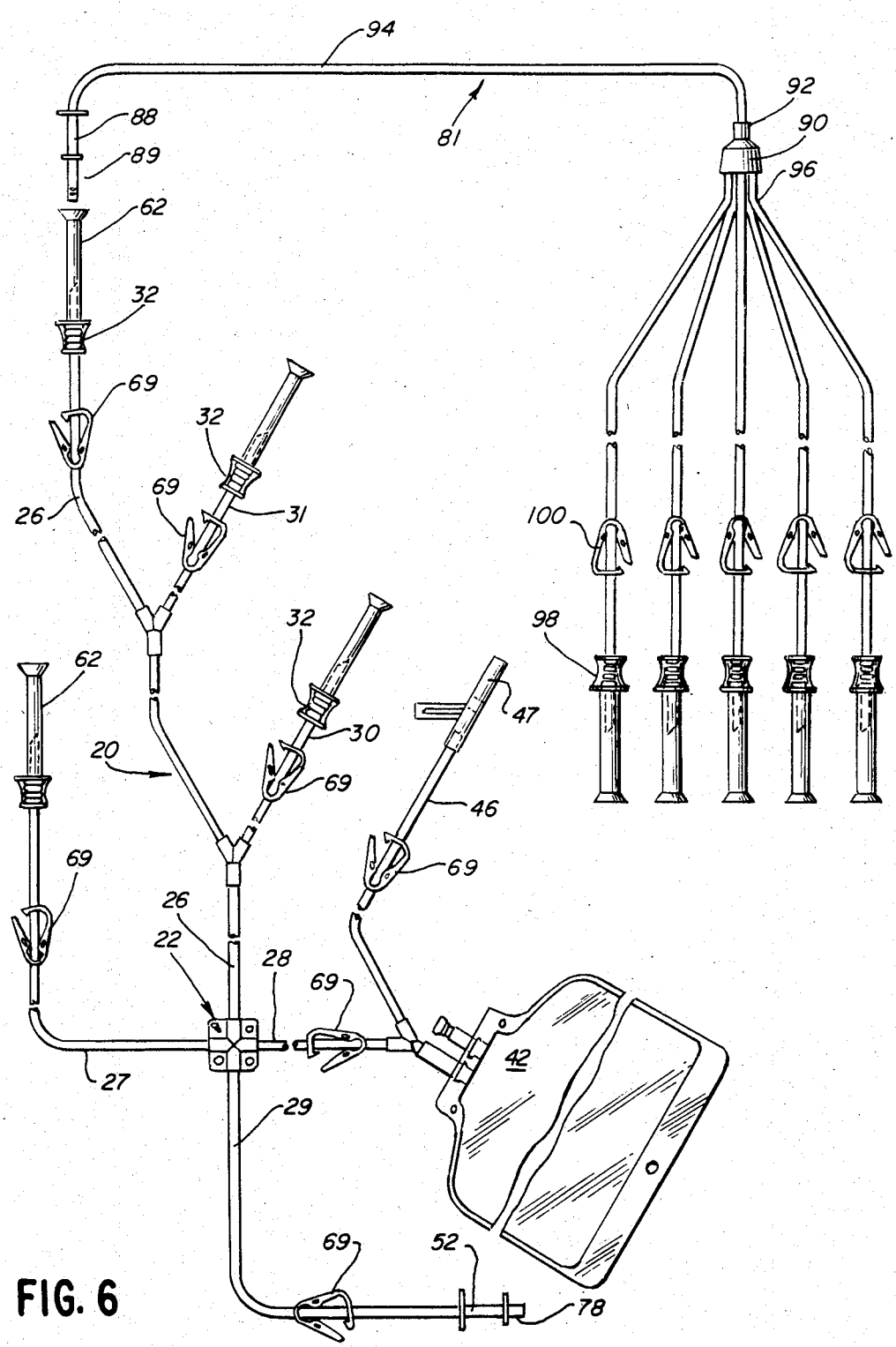
FIG. 6 is a plan view of the flexible-conduit container and set member shown in FIG. 1 with an optionally added five port manifold set assembly.

It should be noted that the various flexible conduits of FIG. 6 are all illustrated in broken form so that their relative lengths are not intended to be shown. The specific selection of their relative lengths is, of course, an entirely routine manner depending upon the nature of dialysis machine with which set 20 is used.

Flexible tubing 29 extends from X connector 22 and communicates at is other end in this particular embodiment with a flanged connector 52, which is capable of receiving a spike of a patient's transfer set. The transfer set, in turn, communicates through a catheter to the patient's peritoneal cavity. Connector 52 and the spike from the transfer set may be so proportioned as to be locked together by a commercially available Connection Shield sold by Travenol Laboratories, Inc., of Deerfield, Ill., and presently used by most CAPD patients in the United States.

Figure 2:
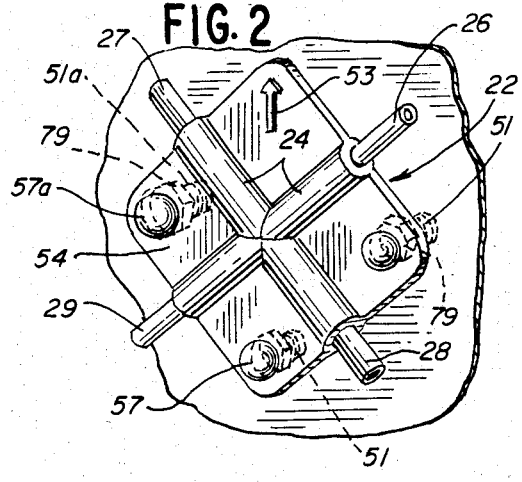
FIG. 2 is a front perspective view of the X connector of the set member, carried on the bracket member of the peritoneal dialysis hardware apparatus of FIG. 1.
Figure 3:
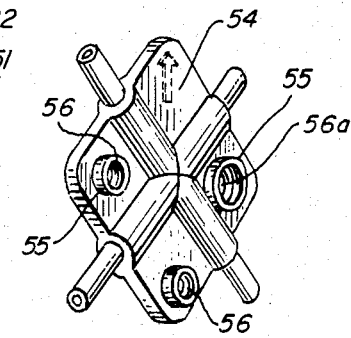
FIG. 3 is a back perspective view of the X connector of FIG. 2.

X connector 22, as particularly shown in FIGS. 2, 3, and 6, defines a flange 54 perforated by a plurality of apertures 56, 56a, typically three in number arranged in triangular array. Aperture 56a is of larger diameter than aperture 56.

As shown particularly in FIG. 2, dialysis apparatus 19 carries a bracket member which comprises three pins 51, 51a positioned in corresponding triangular array to the arrangement of apertures 56, 56a and proportioned so that pins 51, 51a can pass through apertures 56, 56a in snap-fit relation thereto by the action of enlarged beads 57, 57a, to retain X connector 22 in only a single position of orientation on the bracket member defined by pins 51, 51a. This is so because larger pin 51a can only pass through aperture 56a, while the smaller pins 51 will correspondingly enter into snap-fit relation with apertures 56.

Hex nuts 79 are provided as a fixed part of pins 51, 51a to facilitate their placement into threaded holes in the face of apparatus 19 as shown.

Thus, as the user removes set 20 from its box, a great deal of confusion with respect to what line goes where is eliminated by first attaching X connector 22 into its single position of orientation on dialysis apparatus 19. Thereafter, the flexible tubings 26-29 are naturally directed into the direction they should go to reach their intended destination stations, i.e., dialysis solution supply station 34, dialysis solution heating station 38, dialysis solution volume measuring station 44, and finally the patient himself via line 29. One needs only to extend the lines in the direction to which they are naturally pointed by X connector 22, to find the right station to which each flexible tubing is to go.

Sleeves 55 abut hex nuts 79 on the face of apparatus 19 to stabilize X connector 22 as it rests in position of use. Embossed arrow 53 points upwardly when connector 22 is properly mounted.

Figure 4:
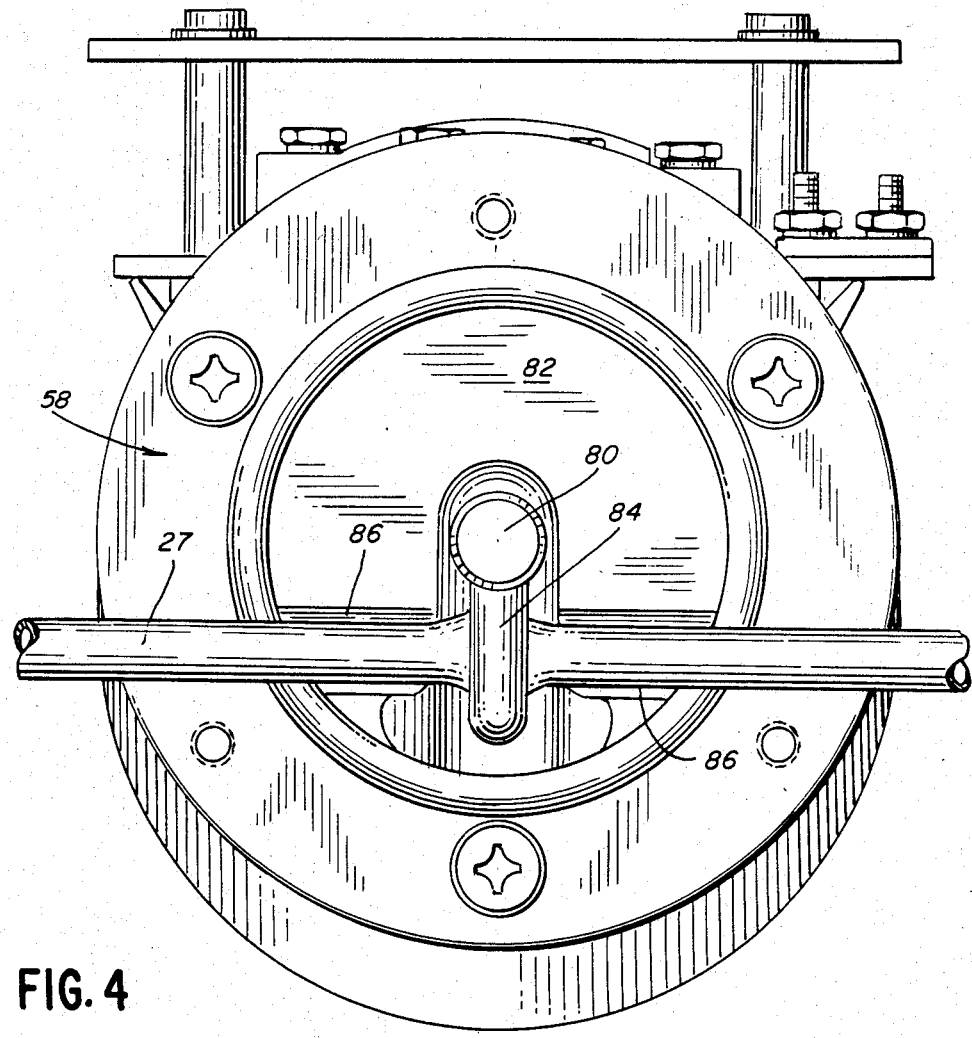
FIG. 4 is an elevational view of a clamp of the apparatus of FIG. 1 used in the valve means for controlling dialysis solution flow around the apparatus.

The respective flexible tubings are threaded through clamp or valve members 58-62, each of said clamps or valves being of the type shown in FIG. 4. As shown, flow through tubing 27 is controlled by clamp 58; flow through tubing 28 is controlled by clamp 60; and flow through tubing 29 is controlled by clamp 59. Flow through tubing 26 is controlled by clamp 61, while flow through branch tubing 30 has a separate control clamp 62, so that bag 36a may flow through tubing 30 and part of tubing 26 even when clamp 61 is closed.

Referring in further detail to FIG. 4, clamp or valve member 58 defines a movable rod 80 which can move in and out from housing 82, carrying side member 84. Tubing, for example tubing 27, fits into clamp member 58, resting in groove 86, being retained therein by side member 84. Inside of housing 82 spring apparatus biases side member 84 and shaft 80 into the closed position, collapsing tubing 27. A gear system, powered by an electric motor, can be actuated to extend shaft and side member 84 outwardly to a position to permit flow through tubing 27, while retraction of shaft 80 and side member 84 shuts off flow in tubing 27.

Figure 5:
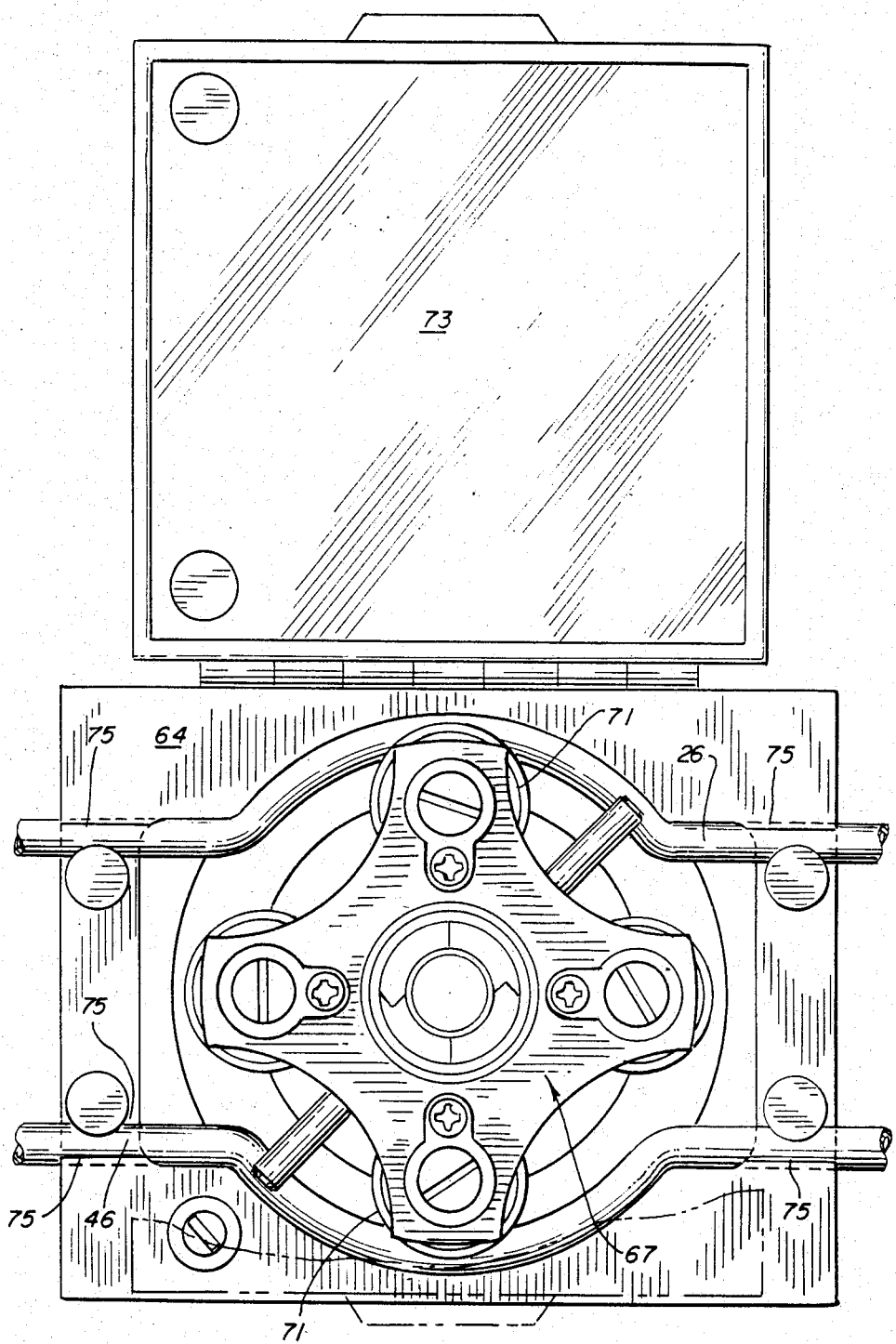
FIG. 5 is an elevational view of the pump station of the apparatus of FIG. 1.

A peristaltic or roller type pump 64 is provided as a pump station, as shown in detail in FIG. 5, with a track for receiving two separate lengths of flexible tubing, namely, tubings 26 and 46. Thus a single pump rotor 67 is provided, having rollers 71, so that pumping action takes place simultaneously in tubings 26, 46, with the nature and amount of fluid and flow being covered by clamps 58–62.

Pump 64 is typically adapted to only operate in one direction, but the separation, opposed mounting of tubings 26 and 46 provides the possibility of simultaneous flow in opposite directions in each tubing relative to the other. Closable, hinged lid 73 is provided to close the pump station 64.

Clips 63 are provided on apparatus 19 to retain tubing of set 20 in position.

Monitor and control panel 66 is provided, and thumb wheel switches 68 for cycle control are also present behind an openable panel as shown (FIG. 1). Appropriate electronics are present for both, controlling the sequence of various cycles and the timing thereof, so that the apparatus of FIGS. 1–6 functions in the manner described below. The device of this invention can be alternatively programmed to operate in Continuous Cycling Peritoneal Dialysis, Continuous Intermittent Peritoneal Dialysis, Intermittent Peritoneal Dialysis, or other modes of operation. The apparatus may also have microprocessor systems for functional checking of the device, and a light and buzzer to indicate any malfunctions, and to disable the system from operation in the event of significant malfunctions.

For functioning power is turned on, and after the dialysis apparatus 19 has passed an internal diagnostics check, an indicator shall display this fact, and all five valves 58–62 are closed. Heater 38 can then be enabled by placing a solution bag upon it. The system then waits for a start/continue button to be pushed in console 66. Upon doing so, an indication that it is in the set-up mode will be displayed and all valves will open. The user then sets up apparatus 19 for the particular peritoneal dialysis treatment modality to be employed by loading set 20 and connecting it with the desired bags.

In FIGS. 1–6, a CCPD treatment modality is set up, with bags 36, 36a, and 40 being connected by spiking to flexible-conduit container and set member 20, with X connector 22 being attached to the bracket comprising pins 51, 51a as shown, and bag 52 of set 20 being placed at volume measuring station 44. Tubing 26, 46 is loaded into pump 64 after priming of the system with solution from bag 40. After priming, manual clamps 69 may be closed until the operating cycles commence.

Tubings 26, 46 are then placed into the occluding roller system of pump 64. Sensing devices may be present to assure that the cycler set tubing has been properly placed into the pump restricting slots 75 to properly engage pump occluding rollers 71, upon closure of the pump door.

Upon a second activation of the start/continue button, all valves 58–62 close again. A monitor systems may be used to indicate that each of the five valves has closed on tubing, so that in the event of a failure to provide proper valving of one of the tubings an alarm will sound. The valve in question can automatically open and wait for proper tubing placement while all other valves remain closed, this being controlled by a microprocessor system.

To begin CCPD treatment, flexible tubing 29 is connected to the patient who, in a CCPD procedure, is carrying peritoneal dialysis solution in his peritoneal cavity. Connector 52 may be opened by removing protector 78 and connected to a peritoneal catheter or transfer set.

As a first, DRAIN, phase, valves 59 and 60 open, permitting draining of spent peritoneal dialysis solution from the patient through line 29, X connector 22, and line 28 into weigh bag 42, which may be a typically three liter solution bag. The final weight, translating to a given solution volume, may be recorded in the memory of a microprocessor system and displayed on console 66 for ultrafiltration calculations.

During the DRAIN phase, the scale in dialysis solution heater station 38 may be monitored to insure that it is maintaining a constant volume, as was preset into the cycler during the set-up procedure. Dialysis solution should not enter or leave upper heater bag 40 during this period of time, and if there is a change of weight, such change of weight is an indication of a misloaded set or another system failure.

Weigh station 44 is also monitored by the microprocessor system for a no-flow condition, so that kinked tubing or other problems can be quickly caught and corrected. The user can set the desired duration of the DRAIN phase into the electronics of the system. When this time has elapsed, the apparatus will proceed to the FILL phase.

In the FILL phase, valve 60 closes, valve 58 opens, and valve 59 remains open. Dialysis solution from bag 40, warmed at heater 38, flows into the peritoneal cavity of the patient through tubing 27, X connector 22, and tubing 29. The scale of station 38 can be monitored by the microprocessor system so that only a preset fill volume passes to the patient, after which valves 58, 59 close. Flow is by gravity, no pump being used for flow to and from the patient.

If the scale in station 38 does not sense a decrease in volume, an alarm will be displayed so that the kinked tubing or other problem can be corrected. Likewise, if the specified time for the fill cycle runs out before the preprogrammed fill volume has been infused, as sensed by the scale means in station 38, an alarm can be sounded to inform the user of this fact.

Following this, the DWELL phase takes place, during which solution resides in the patient, pump 64 is activated, and valves 61, 58 are open, so that solution from bags 36 is pumped to bag 40 in the volume preset into the system by the user. The other valves are closed, particularly valve 59. Simultaneously, solution in bag 2 is pumped through conduit 46 to drain bag 48 or directly to a drain, as may be desired. During the DWELL phase, new solution in bag 40 will be heated at heater station 38, and its volume will be measured by the scale at station 38, for future calculation of ultrafiltration. The DWELL phase proceeds for a time preset by the user at console 66. Once again, each of the scales at stations 38, 44 is monitored after filling and draining is complete, and pump 64 stopped, to insure the stability of readout, showing that there is no leakage of solution into or out of either bags 40, 42. The microprocessor system can also monitor a no-flow condition during the dwell procedure indicating a malfunction in the filling or the draining of bags 40, 42.

As previously described, last bag 36a may contain a higher dextrose concentration for the patient to carry throughout the day in a CCPD procedure, or other medicaments or the like may be included in bag 36a. The microprocessor is given instructions through console 66, as it proceeds through the cycling of the apparatus, to open valve 62 rather than valve 61 in the DWELL phase when it is time to administer bag 36a. Prior to the administration of last bag 36a, left over normal solution existing in solution bag 40 may be drained directly to drain bag 48. Then, solution from last bag 36a is delivered to heater bag 40 for heating.

At the termination of the DWELL phase, a predetermined time, the apparatus recycles back to the DRAIN phase, at which valves 59, 60 are opened for draining of the spent dialysis solution from the patient's peritoneal cavity to the emptied bag 42 through X connector 22.

The apparatus of this invention thus recycles itself through the various phases: the DRAIN phase where fluid flows from the patient to bag 42, the fill phase where liquid flows from bag 40 to the patient's peritoneal cavity, and the DWELL phase where clamp or valve 59 is closed off to isolate the fluid in the peritoneal cavity, and pump 64 operates to both pump a predetermined amount of fresh dialysis solution from station 34 to the heating station 38, and to pump spent dialysis solution from bag 42 through drain line 46. This sequence of cycling can repeat any desired number of times, terminating if desired with dialysis solution fom the "last bag" 36a as programmed by the user on console 66.

The amount of ultrafiltration, i.e., water removed from the patient by the dialysis solution in a given cycle, is calculated by the microprocessor system of the apparatus by subtracting the weight of solution administered to the patient from bag 40 in the FILL phase from the weight of solution recovered into bag 42 in the next DRAIN phase. This difference may then be displayed at console 66 for a direct ultrafiltration readout.

When it is desired to provide access to a larger supply of solution, a five port manifold set 81 as shown at FIG. 6 may be brought into communication with the spike 32 on the end of tubing 26, 30, or 31 by removal of protector members 62, 89, and penetration of spike 32 into double flange connector member 88, similar in design if desired to dialysis member 52. This connection may also be protected by the use of a clamshell type protector member similar to those sold by Travenol Laboratories, Inc. and previously described.

As shown in FIG. 6, a single molded piece 90 defines an inlet port 92 for tubing 94 and five interconnecting apertures to which tubings 96 are connected so that there is interconnecting flow between tubing 94 and tubings 96. The ends of tubings 96 terminate in spike-type connectors 98 of conventional design and also carry pinch clamps 100. Thus, by this technique, any number of added connector spikes may be attached to set 20 of this invention for use of the set, for example, with an intermittent peritoneal dialysis procedure using large quantities of dialysis solution.

The above has been offered for illustrative purposes only, and it is not intended to limit the scope of the invention of this application, which is as defined in the claims below.

That which is claimed is:

1. In automated peritoneal dialysis apparatus having dialysis solution supply station, a dialysis solution heating station, a dialysis solution volume measuring station, a pump station for moving said dialysis solution, and valve means for controlling dialysis solution flow around said apparatus, the improvement comprising, in combination:

bracket means for receiving and holding a multiple fluid flow junction connector of a flexible-conduit set member carried by said apparatus, said bracket means being adapted to hold said multiple junction connector in only a single position of orientation, whereby flexible conduits of said set member extending from said multiple junction connector are naturally directed toward their intended destination stations;

wherein said bracket means defines a plurality of pins to pass through corresponding apertures of a mounted multiple junction connector for retention thereof in a single position of orientation in which said pins define enlarged outer ends to provide snap-fit retention for said mounted conector and wherein said pins are disposed in a triangular pattern.

2. The apparatus of claim 1 in which said pump station defines a multiple opposed tracks means for installing separate tubing sections of said set member and a single pump rotor member for simultaneously pumping fluid through both of said tubing sections.

3. In automated peritoneal dialysis apparatus having a dialysis solution supply station, a dialysis solution heating station, a dialysis solution volume measuring station, a pump station for moving said dialysis solution, valve means for controlling dialysis solution flow around said apparatus, and a flexible-conduit set member carried by said apparatus with containers connected to said set member respectively carried by said dialysis solution supply station, dialysis solution heating station, and dialysis solution volume measuring station, the improvement comprising, in combination:

bracket means for receiving and holding an X connector of said flexible conduit set member carried by said apparatus, an X connector as part of said set member carried on said bracket means, said X connector providing four way intercommunication with flexible tubings respectively communicating with (1) the dialysis solution supply station, (2) the dialysis solution heating station, (3) the dialysis solution volume measuring station, and (4) a connector adapted for flow communication with the peritoneal cavity of the patient, said X connector and bracket means being adapted to cause the X connector to be holdable in only a single position of orientation in the bracket means, whereby the flexible tubings communicating with the X connector and extending therefrom are naturally directed toward their intended destination stations.

4. The apparatus of claim 3 in which said bracket means defines a plurality of pins of differing diameter, and said X connector comprises a plurality of apertures of corresponding, differing diameter, with said pins penetrating said apertures.

5. The apparatus of claim 4 in which three of said pins are present, disposed in a triangular pattern.

6. The apparatus of claim 5 in which said pins define enlarged outer ends to provide snap-fit retention of the X connector.

7. The apparatus of claim 4 in which said pump station defines track means for installing separate tubing sections of said container and set member into said pump station, and a single pump rotor member for simultaneously pumping fluid through both of said tubing sections, one of said tubing sections installed in said track means communicating between the X connector and the dialysis solution supply station, and another of said separate tubing sections communicating from the dialysis solution volume measuring station to drain.

8. A flexible-conduit set member, which comprises:
a flexible container;
flexible tubing communicating between said container and an X connector;
other flexible tubings communicating with said X connector and terminating in coupler members, one of said other flexible tubings defining at least two connected branch tubings terminating in coupler members, one of said container and its connecting flexible tubing also defining a branching tubing extending therefrom;
wherein said X connector defines flange means, said flange means defining a plurality of apertures of differing size, to permit installation of said X connector on a bracket of a peritoneal dialysis apparatus in only a single position of orientation.

9. The container and set member of claim 8 in which one of the other flexible tubings or a connected branch tubing thereto is connected to a manifold tube, said manifold tube being connected at its other end to a one-piece, molded plastic manifold, a plurality of manifold branch tubes being connected to said plastic manifold, said manifold branch tubes terminating in coupler members and carrying flow clamps.

10. The flexible conduit set member of claim 8 in which one side of said X connector defines sleeves surrounding said apertures and projecting outwrdly to stabilize the X connector as it rests against a flat surface in position of use.

* * * * *